United States Patent
Nagda et al.

(10) Patent No.: US 8,856,963 B2
(45) Date of Patent: Oct. 14, 2014

(54) FINGER PROTECTOR

(71) Applicants: Sameer Nagda, Alexandria, VA (US); Samir Sodha, Monroe, NY (US)

(72) Inventors: Sameer Nagda, Alexandria, VA (US); Samir Sodha, Monroe, NY (US)

(73) Assignee: Sam Innovations, LLC, Alexandria, VA (US)

( * ) Notice: Subject to any disclaimer, the term of this patent is extended or adjusted under 35 U.S.C. 154(b) by 0 days.

(21) Appl. No.: 13/681,395

(22) Filed: Nov. 19, 2012

(65) Prior Publication Data

US 2014/0137306 A1    May 22, 2014

(51) Int. Cl.
*A41D 13/08*    (2006.01)

(52) U.S. Cl.
CPC ..................................... *A41D 13/08* (2013.01)
USPC ............................................................. 2/21

(58) Field of Classification Search
USPC ..................... 2/21, 163, 161.6, 160; 128/880; 223/101; 606/148, 144; 294/25; D3/29
See application file for complete search history.

(56) References Cited

U.S. PATENT DOCUMENTS

| | | | | |
|---|---|---|---|---|
| 72,751 | A | * | 12/1867 | Niles .............................. 223/101 |
| 88,708 | A | * | 4/1869 | Hall .............................. 30/123.5 |
| 107,420 | A | * | 9/1870 | Spencer ........................ 223/101 |
| 136,157 | A | * | 2/1873 | Hall .............................. 30/123.5 |
| 366,102 | A | * | 7/1887 | Hoeneman ...................... 30/291 |
| 645,550 | A | * | 3/1900 | Clark ........................... 30/123.5 |
| 651,796 | A | * | 6/1900 | Crandall ......................... 30/291 |
| 738,061 | A | * | 9/1903 | Penny .............................. 30/298 |
| 805,297 | A | * | 11/1905 | Huntington .................... 223/101 |
| 922,954 | A | * | 5/1909 | Rives ............................... 294/25 |
| 1,109,796 | A | * | 9/1914 | Sills ................................. 294/25 |
| 1,235,605 | A | * | 8/1917 | Sauer ............................. 242/149 |
| 1,261,706 | A | * | 4/1918 | Condley et al. .................. 294/25 |
| 1,359,717 | A | * | 11/1920 | McCarthy ........................ 294/25 |
| 1,980,635 | A | * | 11/1934 | Rasmussen et al. ................. 2/21 |
| 2,070,506 | A | * | 2/1937 | Bevill .................................. 2/21 |
| 2,285,981 | A | * | 6/1942 | Johns .................................. 2/21 |
| 2,348,962 | A | | 5/1944 | Davis |
| 2,379,624 | A | * | 7/1945 | Chisnell .......................... 294/25 |
| 2,415,957 | A | * | 2/1947 | McCormack ................. 223/101 |
| 2,432,579 | A | * | 12/1947 | Lloyd ............................ 223/101 |
| 2,541,606 | A | * | 2/1951 | Palmer .............................. 87/52 |
| 2,717,799 | A | * | 9/1955 | Jones ............................... 294/25 |
| 3,191,824 | A | * | 6/1965 | Burr .............................. 223/101 |
| 3,511,242 | A | * | 5/1970 | Agnone ......................... 606/148 |
| 3,728,736 | A | * | 4/1973 | Pugh .................................. 2/21 |
| 4,037,433 | A | * | 7/1977 | Weber ............................. 66/1 A |
| 4,097,931 | A | | 7/1978 | Hirose |
| 4,127,222 | A | * | 11/1978 | Adams .......................... 223/101 |
| 4,796,302 | A | | 1/1989 | Davis |
| 4,858,245 | A | | 8/1989 | Sullivan |
| 4,873,998 | A | | 10/1989 | Joyner |
| 4,995,119 | A | | 2/1991 | Codkind |
| 5,070,543 | A | | 12/1991 | Beck |
| 5,234,142 | A | | 8/1993 | Loewen |
| 5,423,090 | A | | 6/1995 | Gimbel |
| 5,428,841 | A | | 7/1995 | Stein |
| 5,496,337 | A | | 3/1996 | Brown |
| 5,507,041 | A | * | 4/1996 | Wright ............................... 2/21 |

(Continued)

*Primary Examiner* — Amy Vanatta
(74) *Attorney, Agent, or Firm* — Richards Patent Law P.C.

(57) ABSTRACT

A finger protector includes: a pad; a protective layer disposed along the outer surface of the pad; one or more suture-engaging mechanisms disposed on the outer surface of the protective layer; and one or more securing mechanisms adapted to releasably secure the pad, protective layer, and one or more suture-engaging mechanisms to a user's finger.

22 Claims, 4 Drawing Sheets

(56) References Cited

U.S. PATENT DOCUMENTS

| | | | |
|---|---|---|---|
| 5,522,821 A * | 6/1996 | Brown | 606/148 |
| 5,617,952 A | 4/1997 | Kranendonk | |
| 6,110,186 A * | 8/2000 | Rizvi | 606/148 |
| 6,128,778 A | 10/2000 | Castagneri | |
| 6,243,868 B1 | 6/2001 | Wanzenried | |
| 7,249,385 B2 | 7/2007 | Schukraft | |

* cited by examiner

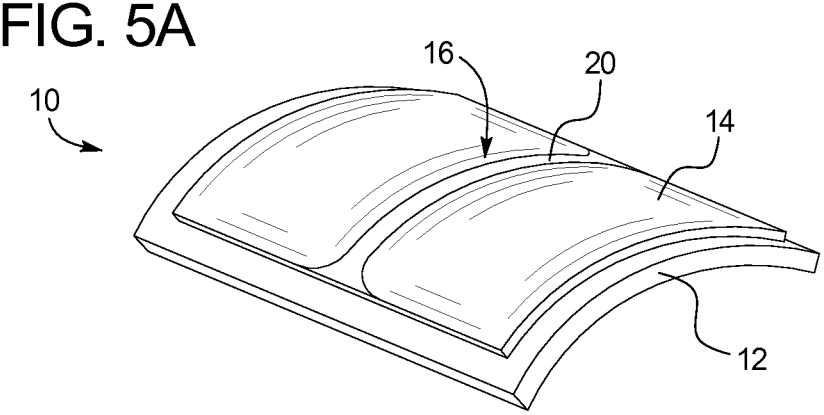
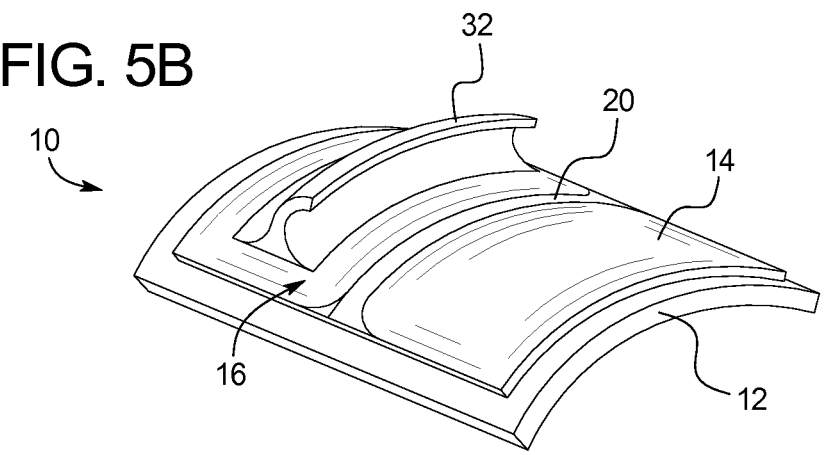
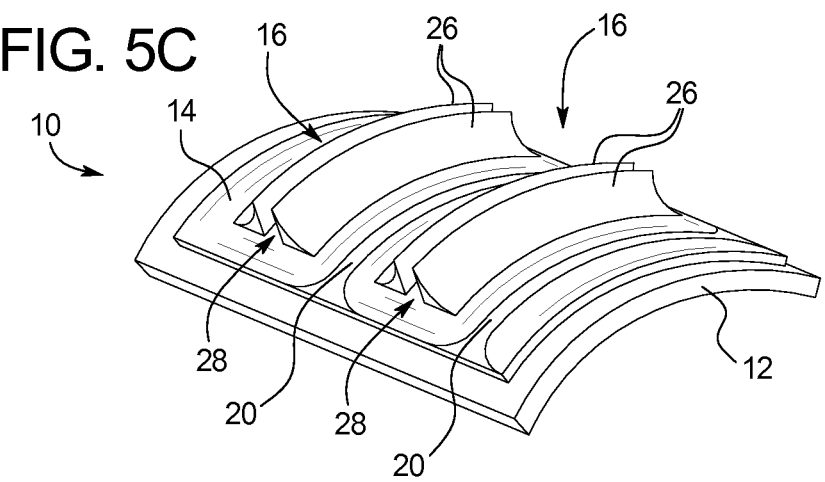

FINGER PROTECTOR

CROSS-REFERENCE TO RELATED APPLICATIONS

This application incorporates by reference and claims priority to U.S. Provisional Patent Application No. 61/561,873 filed Nov. 19, 2011.

BACKGROUND OF THE INVENTION

The present subject matter relates generally to a finger protector to be worn over surgical gloves. More specifically, the present subject matter discloses a finger protector to be worn over or under surgical gloves to protect the wearer's finger when tensioning sutures or tying knots with suture products.

Suturing is a common procedure for a number of surgeons and other qualified medical professionals. The suturing process includes placing one or more sutures attached to a needle using a needle holder. The needle is passed through the patient's flesh on one side of an open wound, advanced to the opposing side of the wound, pulled through the skin, and then the suture thread is tied into a knot.

The suture thread is typically formed from a strong, synthetic material, generally in a relatively small diameter. Due to the strength of the material and the diameter of the thread, handling of the thread, particularly tensioning and tying the thread into a knot, can injure the medical professional's fingers, particularly the area of the finger surrounding the distal interphalangeal joint. It is not uncommon for the tensioning of the thread and the typing of knots to leave abrasions or even small cuts in the surgeon's fingers. This happens even through the surgical gloves typically worn when suturing. In fact, the sutures can cut through the surgical gloves, limiting the usefulness of the gloves to act as a shield between the patient and the medical professional.

Individual procedures may involve the placement of a large number of sutures and a particular medical professional may perform numerous suturing procedures in a given day. As a result, over time, the suturing process can take a toll on a surgeon's fingers. Accordingly, medical professionals would benefit from having a finger shield that would help to save their fingers from the damage that occurs during repeated suturing.

One concern regarding the use of a finger shield when suturing is that the quality and efficiency of the medical professional's ability to suture is highly dependent on the surgeon's manual dexterity. As a result, bulky shields or those that otherwise diminish a surgeon's ability to manipulate the sutures are unlikely to be widely used by medical professionals.

Accordingly, there is a need for a finger protector to be worn over or under surgical gloves, as described and claimed herein.

BRIEF SUMMARY OF THE INVENTION

The present disclosure provides a finger protector for use in suturing and other medical procedures. Various examples of the finger protector are provided herein.

In a preferred embodiment, a finger protector includes a pad covered by a protective layer. The protective layer is typically formed from a durable material, preferably a hard plastic or similar material. The protective layer includes one or more suture-engaging mechanisms, such as ridges or grooves, adapted to assist the wearer's proprioception and dexterity with respect to the suture process. In certain embodiments, a pair of adjustable Velcro straps is used to hold the finger guard in place. In others, the finger guard may be held in place with an elastic ring. Of course, there are numerous means for holding the finger protector in place on the user's finger, as will be recognized by those skilled in the art based on the disclosures provided herein. For example, the finger protector may be secured to the user's finger using a releasable adhesive.

As described, the finger protector includes one or more suture-engaging mechanisms, typically ridges or grooves, to assist the user in locating and gripping a suture or suture thread. Numerous configurations may be used, but the preferred embodiments include one to three suture-engaging mechanisms along the length of the protective layer. Locating the suture-engaging mechanisms along the protective layer helps to keep the sutures and suture thread in contact with the protective layer is use, which protects the user's fingers from injury and/or protects the user's surgical gloves from damage.

The inclusion of the pad beneath the protective layer cushions the wearer's finger from the typically harder protective layer. This improves the comfort of the device and enables the wearer to use the device over longer periods of time without discomfort. In preferred embodiments, the pad may include a portion formed from foam, gel, or other soft material. Further, the pad may be larger than the outer protective layer, which provides more protection at the periphery of the protective layer, helping to prevent the protective layer from digging into the wearer's finger.

The finger protector may be offered in numerous sizes and configurations particularly adapted for the finger to be protected. For example, the finger protector may be offered in left-hand and right-hand versions, versions for specific fingers or thumbs, and varying sizes. Of course, it is also understood that a universal protector may be used that is adaptable to a wide range of finger sizes and uses. In a preferred embodiment, the finger protector is adapted to protect the radial side of the distal interphalangeal joint (DIP joint) of the index finger. For example, the protective layer may cover from approximately 1 cm proximal to the DIP joint to 1 cm distal to the same joint. In another preferred embodiment, the finger protector is adapted to protect the ulnar side of the DIP joint of the pinky finger. Typical dimensions for the finger protector may be 5-20 mm in length by 5-15 mm wide by 1-3 mm thick. In addition, the pad and protective layer may be curved to more closely conform to the shape of the wearer's finger.

It is contemplated that the finger protector may be adapted to be worn under or on top of standard surgical gloves. When worn over surgical gloves, the finger protector(s) can be applied and removed multiple times during the same procedure. Wearing the finger protector over the surgical glove further protects the glove itself from damage by the sutures and suture threads.

In one example, a finger protector includes: a pad; a protective layer disposed along the outer surface of the pad; one or more suture-engaging mechanisms disposed on the outer surface of the protective layer; and one or more securing mechanisms adapted to releasably secure the pad, protective layer, and one or more suture-engaging mechanisms to a user's finger. In certain embodiments, the pad may be formed from a foam or gel material. The protective layer may be formed from a rigid polymeric material. The pad may be both longer and wider than the protective layer to better isolate the protective layer from the user's finger. The one or more suture-engaging mechanisms may include at least one groove in the protective layer, at least one ridge formed in the protective layer, at least one hook disposed along the outer surface of the protective layer or any combination thereof.

Further, the one or more securing mechanisms may include at least one strap adapted to secure the finger protector to a user's finger. The strap may be adjustable and reusable and may include hook and loop fasteners to secure the straps in place along the finger protector. The finger protector may further include a second strap including hook and loop fasteners. The securing mechanisms may further or alternatively include a releasable adhesive disposed along the back of the pad. Even further, the one or more securing mechanisms may include at least one band adapted to secure the finger protector to a user's finger. The band may be an elastic band. In some embodiments, there may be a second elastic band. The one or more securing mechanisms may further include an adhesive disposed along the back of the pad either as the primary securing mechanism or to supplement another securing mechanism.

In another version of the finger protector, the finger protector includes: a foam pad; a rigid polymeric protective layer disposed along the outer surface of the pad; at least two suture-engaging mechanisms disposed on the outer surface of the protective layer; and one or more securing mechanisms adapted to releasably secure the pad, protective layer, and suture-engaging mechanisms to a user's finger. The suture-engaging mechanisms may include any number of grooves, ridges, and hooks disposed on the outer surface of the protective layer.

An advantage of the finger protector provided herein is that it protects a wearer's fingers from injury during the suturing process.

Another advantage of the finger protector provided herein is that it improves the wearer's dexterity with respect to the suturing process.

A further advantage of the finger protector provided herein is it is disposable and inexpensive to make.

Another advantage of the finger protector provided herein is it can be worn over surgical gloves to protect both the wearer's fingers and the surgical gloves themselves, helping to preserve the protective barrier between the medial professional and the patient.

Yet another advantage of the finger protector provided herein is it can be worn under surgical gloves.

Still another advantage of the finger protector provided herein is the ridge or indentation found in some embodiments of the finger protector improves the wearer's proprioception and handling of the suture.

Another advantage of the finger protector provided herein is that it does not interfere with the wearer's finger motion as it fits onto the finger without interfering with the use of the distal interphalangeal joint and can be removed and applied easily.

Yet another advantage of the finger protector provided herein is certain versions of the protector do not interfere with the user's fingertip proprioceptive sense as they do not cover the fingertip and allow the wearer to maintain this important ability during surgery. The finger protector protects the area that is at highest risk for skin injury, while leaving the rest of the digit and hand free for the wearer's comfort.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIGS. 5a-5c are front side perspective views of various embodiments of suture-engaging mechanisms and configurations.

DETAILED DESCRIPTION OF THE INVENTION

Figure 1:
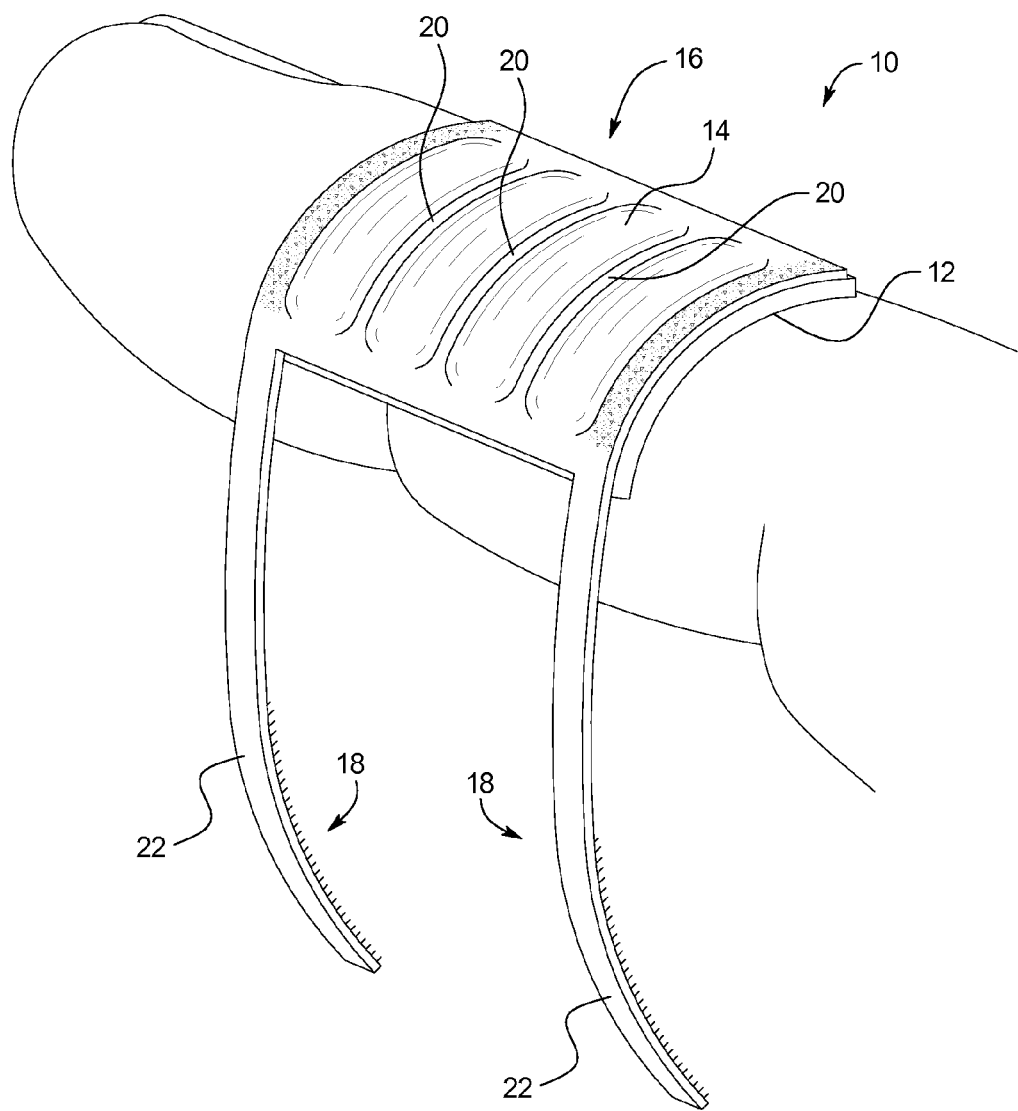
FIG. 1 is a front side perspective view of an embodiment of a finger protector.

FIG. 1 illustrates an example of a finger protector 10. As shown in FIG. 1, the finger protector 10 includes a pad 12, a protective layer 14, three suture-engaging mechanisms 16, and a securing mechanism 18.

As shown, the pad 12 used in the example shown in FIG. 1 is a foam pad 12 approximately 1.5 mm thick. In use, the soft foam material rests securely against the wearer's finger, for example, along the radial side of the distal interphalangeal joint (DIP joint) of the index finger or the ulnar side of the DIP of the pinky finger. Because the pad 12 is slightly larger than the protective layer 14 above it, the pad 12 protects the wearer's finger from being irritated by the protective layer 14. The pad 12 may be formed from any material that cushions or protects the wearer's finger from the typically harder and more resilient protective layer 14. For example, the pad 12 may be formed from or incorporate a polymeric or gel material, though any of numerous materials may be used. Further, reusable versions of the finger protector 10 may incorporate more substantial and durable pads 12, while disposable versions of the finger protector 10 may incorporate disposable pads 12.

The protective layer 14 shown in FIG. 1 is a rigid outer layer located above the pad 12. In this example, the protective layer 14 is a relatively thin polymeric shield that protects the wearer's finger from the interaction with the sutures, suture threads, or similar materials. The hard shell formed by the protective layer 14 may be shaped to more closely conform to the shape of the wearer's finger. As further shown, the suture-engaging mechanisms 16 are three grooves 20 disposed in the protective layer 14. The grooves 20 are sized and shaped to interact with suture products to improve the handling, tying, and tensioning of the suture. For example, sutures and suture threads may fit into the grooves 20 to enable the prevent slippage and improve the wearer's proprioception with respect to the suture products.

In the example shown, there are three grooves 20 forming the suture-engaging mechanisms 16; however, it is contemplated that there may be any number of grooves 20 disposed on the outer protective layer 14, as described further herein. For example, some embodiments of the finger protector 10 may include a single groove 20 and others include two grooves 20. Other shapes and configurations of suture-engaging mechanisms 16 are contemplated, as described further herein, particularly with respect to FIGS. 5a-5e.

In the example shown in FIG. 1, the securing mechanism 18 includes a pair of straps 22 that wrap around the wearer's finger and secure the straps 22 to themselves using hook and loop fasteners, or the like. Using hook and loop fasteners, or other releasable and reusable fasteners, enables the finger protector 10 to be easily removed and reattached multiple times without diminution of the integrity of the finger protector 10. Of course, in disposable versions of the finger protector 10, the securing mechanism 18 may one time use. For example, an adhesive may be used to secure the straps 22. Further, an adhesive may primarily or secondarily secure the finger protector 10 to the wearer's finger or the wearer's surgical glove, as described in further detail with respect to FIG. 4. Of course, numerous versions of the securing mechanism 18 are contemplated, as described further with respect to FIGS. 2-4.

Figure 2:
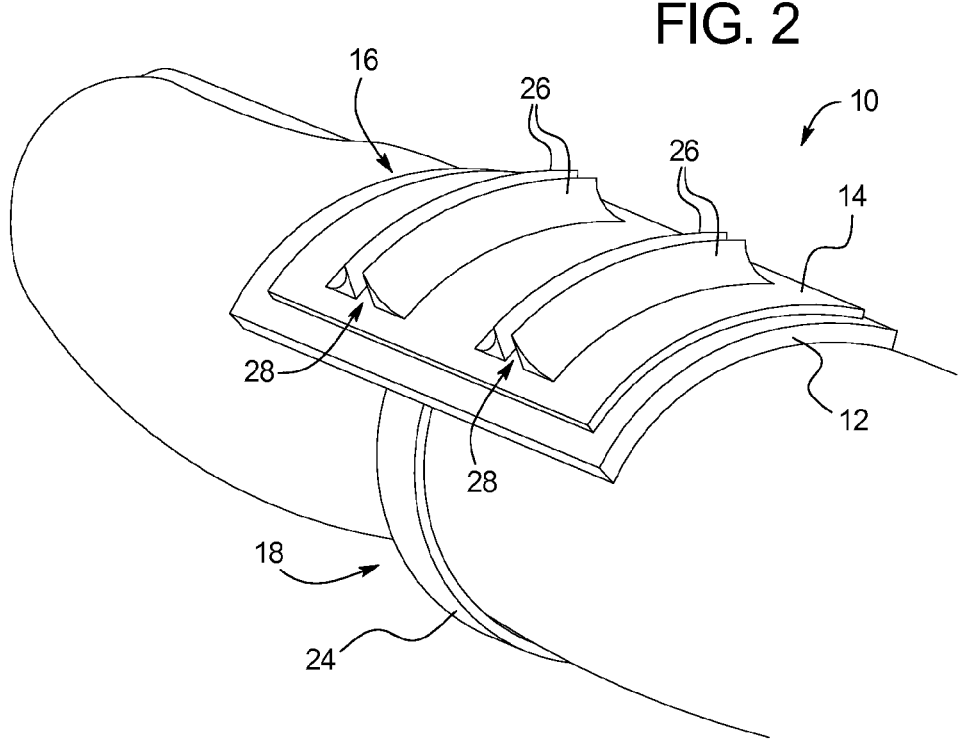
FIG. 2 is a front side perspective view of another embodiment of a finger protector.
Figure 3:
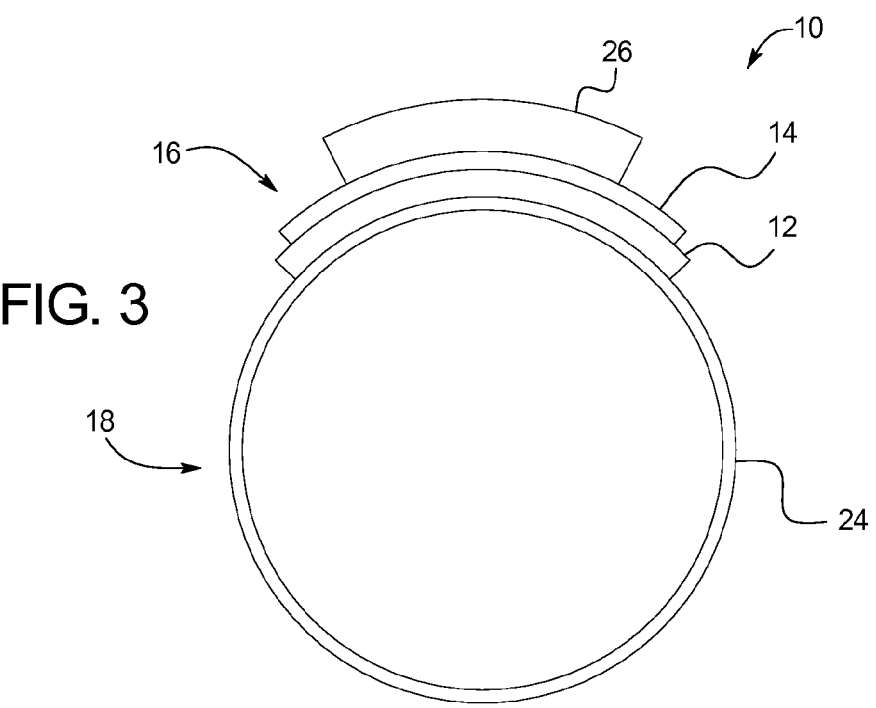
FIG. 3 is a side view of the finger protector shown in FIG. 2.

Turning now to FIGS. 2 and 3, an example of the finger protector 10 is shown in which the securing mechanism 18 is an elastic ring 24 that may fit securely around the wearer's finger to secure the finger protector 10 in place. It is understood that the elastic ring 24 may be of any width that is secure and comfortable for the user. For example, a wider elastic ring 24 may be more secure. In other embodiments, the finger protector 10 may include a pair of elastic rings 24 that may fit on either side of the finger's DIP joint.

As further shown in FIGS. 2 and 3, the suture-engaging mechanisms 16 in this embodiment include two pairs of raised ridges 26 forming channels 28 into which the suture products may be secured. The raised ridges 26 perform a function similar to the recessed grooves 20 shown in FIG. 1 and, again, may be provided in any number and configuration as appropriate for interaction with suture products.

Figure 4:
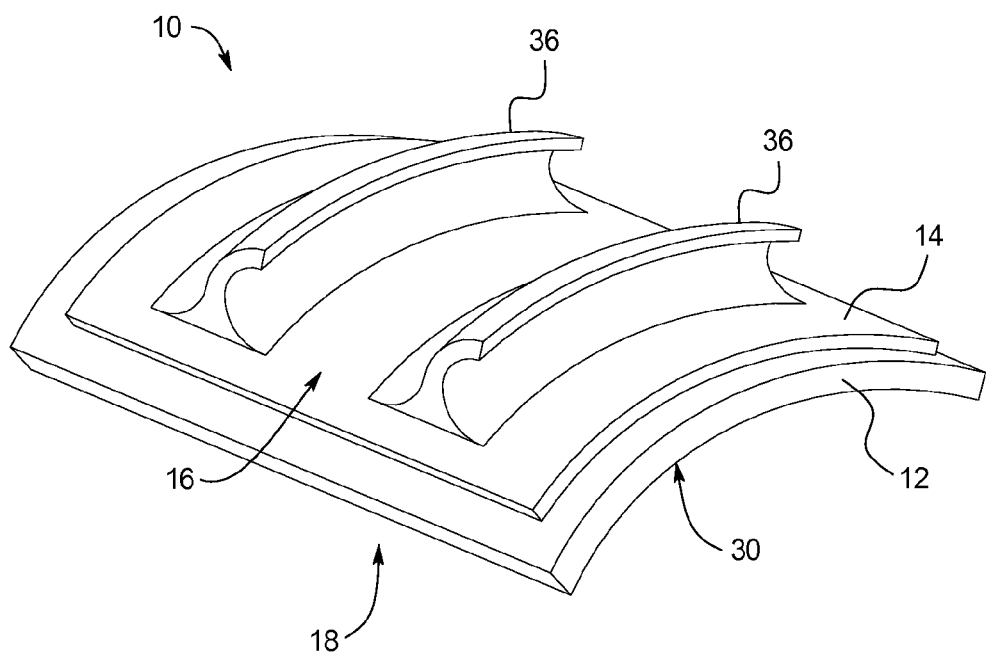
FIG. 4 is a front side perspective view of another embodiment of a finger protector.

FIG. 4 illustrates an example of the finger protector 10 in which the primary securing mechanism 18 is an adhesive on the back surface 30 of the pad 12. Such an embodiment may be most appropriate for use over a surgical glove. As further shown in FIG. 4, the suture-engaging mechanisms 16 include two hooks 32 disposed on the top surface of the outer protective layer 14. The hooks 32 may provide an even stronger engagement for the suture products than either the grooves 20 or ridges 26.

FIGS. 5a-5e provide examples of various configurations of suture-engaging mechanisms 16 in use on examples of finger protectors 10. In FIG. 5a, the finger protector 10 includes a suture-engaging mechanism 16 comprising a single groove 20. In FIG. 5b, the finger protector 10 includes suture-engaging mechanisms 16 including a single groove 20 and a single adjacent hook 32. FIG. 5c illustrates an example in which the suture-engaging mechanisms 16 include a pair of grooves 20 and a pair of ridges 26. It is believed that the various examples of the suture-engaging mechanisms 16 provided herein will be broadly indicative of varied types of suture-engaging mechanisms 16 that may be employed in a finger protector 10.

It should be noted that various changes and modifications to the presently preferred embodiments described herein will be apparent to those skilled in the art. Such changes and modifications may be made without departing from the spirit and scope of the present invention and without diminishing its attendant advantages.

We claim:

1. A finger protector comprising:
a foam pad;
a protective layer disposed along an outer surface of the pad;
one or more suture-engaging mechanisms disposed on an outer surface of the protective layer; and
one or more securing mechanisms adapted to releasably secure the pad, protective layer, and one or more suture-engaging mechanisms to a user's finger,
wherein the protective layer has a width and a length and the one or more suture-engaging mechanisms includes at least one groove or ridge extending parallel to the width of the protective layer, wherein the groove or ridge is perpendicular to the length of the user's finger when the finger protector is secured to the user's finger.

2. The finger protector of claim 1 wherein the protective layer is formed from a rigid polymeric material.

3. The finger protector of claim 2 wherein the pad is longer and wider than the protective layer.

4. The finger protector of claim 1 wherein the one or more suture-engaging mechanisms includes at least two linear ridges formed in the protective layer, wherein the two linear ridges define a channel extending parallel to the width of the protective layer.

5. The finger protector of claim 1 wherein the one or more suture-engaging mechanisms includes at least one linear ridge formed in the protective layer, wherein the linear ridge extends parallel to the width of the protective layer.

6. The finger protector of claim 1 wherein the one or more suture-engaging mechanisms includes at least one hook disposed along the outer surface of the protective layer, wherein the hook extends parallel to the width of the protective layer.

7. The finger protector of claim 1 wherein the one or more securing mechanisms includes at least one strap adapted to secure the finger protector to a user's finger.

8. The finger protector of claim 7 wherein the strap is adjustable and reusable.

9. The finger protector of claim 8 wherein the strap includes hook and loop fasteners to secure the straps in place along the finger protector.

10. The finger protector of claim 9 wherein the one or more securing mechanisms includes a second strap including hook and loop fasteners.

11. The finger protector of claim 9 wherein the one or more securing mechanisms include a releasable adhesive disposed along the back of the pad.

12. The finger protector of claim 1 wherein the one or more securing mechanisms includes at least one band adapted to secure the finger protector to a user's finger.

13. The finger protector of claim 12 wherein the band is an elastic band.

14. The finger protector of claim 12 further including a second elastic band.

15. The finger protector of claim 1 wherein the one or more securing mechanisms include an adhesive disposed along the back of the pad.

16. A finger protector comprising:
a pad;
a protective layer disposed along an outer surface of the pad;
one or more suture-engaging mechanisms disposed on an outer surface of the protective layer; and
one or more securing mechanisms adapted to releasably secure the pad, protective layer, and one or more suture-engaging mechanisms to a user's finger,
wherein the protective layer has a width and a length and the one or more suture-engaging mechanisms includes at least one groove or ridge extending parallel to the width of the protective layer, wherein the groove or ridge is perpendicular to the length of the user's finger when the finger protector is secured to the user's finger.

17. The finger protector of claim 16 wherein the one or more suture-engaging mechanisms include a pair of grooves on the outer surface of the protective layer.

18. The finger protector of claim 16 wherein the one or more suture-engaging mechanisms includes at least one linear ridge formed in the protective layer, wherein the linear ridge extends parallel to the width of the protective layer.

19. The finger protector of claim 16 wherein the one or more suture-engaging mechanisms includes at least two linear ridges formed in the protective layer, wherein the two linear ridges define a channel extending parallel to the width of the protective layer.

20. The finger protector of claim 16 wherein the one or more suture-engaging mechanisms includes at least one hook disposed along the outer surface of the protective layer, wherein the hook extends parallel to the width of the protective layer.

21. The finger protector of claim 16 wherein the pad is a foam pad.

22. The finger protector of claim 16 wherein the pad includes a gel material.

\* \* \* \* \*